(12) United States Patent
Kojima

(10) Patent No.: US 11,612,041 B2
(45) Date of Patent: Mar. 21, 2023

(54) LIGHT SOURCE DEVICE, MEDICAL OBSERVATION SYSTEM, ILLUMINATION METHOD, AND COMPUTER READABLE RECORDING MEDIUM

(71) Applicant: Sony Olympus Medical Solutions Inc., Tokyo (JP)

(72) Inventor: Koji Kojima, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 504 days.

(21) Appl. No.: 16/747,538

(22) Filed: Jan. 21, 2020

(65) Prior Publication Data

US 2020/0305259 A1 Sep. 24, 2020

(30) Foreign Application Priority Data

Mar. 19, 2019 (JP) .............................. JP2019-051418

(51) Int. Cl.
*H05B 47/00* (2020.01)
*H05B 47/17* (2020.01)
(Continued)

(52) U.S. Cl.
CPC ......... *H05B 47/17* (2020.01); *A61B 1/00006* (2013.01); *A61B 1/05* (2013.01); *A61B 1/0638* (2013.01); *A61B 1/0655* (2022.02); *A61B 1/0669* (2013.01); *A61B 1/07* (2013.01); *A61B 5/0051* (2013.01); *H05B 45/22* (2020.01)

(58) Field of Classification Search
CPC ...... H05B 47/17; H05B 47/105; H05B 45/20; H05B 47/12; A61B 1/00006; A61B 1/05; A61B 1/0638; A61B 1/0669; A61B 1/07; A61B 5/0051; A61B 5/4803; Y02B 20/40
See application file for complete search history.

(56) References Cited

U.S. PATENT DOCUMENTS

| 2009/0085901 A1* | 4/2009 | Antony | H05B 47/17 345/211 |
| 2012/0075449 A1* | 3/2012 | Yasuda | A61B 1/0638 348/E7.085 |

(Continued)

FOREIGN PATENT DOCUMENTS

| JP | 2000166867 A | 6/2000 |
| JP | 6249909 B2 | 12/2017 |
| WO | WO-2015005277 A1 | 1/2015 |

*Primary Examiner* — Gerald J Sufleta, II
(74) *Attorney, Agent, or Firm* — Xsensus LLP

(57) ABSTRACT

A light source device includes: light sources; a detector configured to detect light amounts; and a processor configured to: control the light sources to emit light beams by applying a pulse current with a pulse width larger than a predetermined pulse width to the light sources before the processor makes a shift to a strobe observation mode; set a pulse current value at which a ratio of the light amounts of the light beams emitted by the plurality of light sources becomes a predetermined ratio for the plurality of light sources based on a detection result detected by the detector under a state where the pulse current with the pulse width larger than the predetermined pulse width is applied to the plurality of light sources; and make the shift to the strobe observation mode while maintaining the pulse current value for realizing the predetermined ratio.

4 Claims, 6 Drawing Sheets

(51) Int. Cl.
  *A61B 1/06*  (2006.01)
  *A61B 1/00*  (2006.01)
  *A61B 1/07*  (2006.01)
  *A61B 5/00*  (2006.01)
  *A61B 1/05*  (2006.01)
  *H05B 45/22*  (2020.01)

(56) References Cited

U.S. PATENT DOCUMENTS

| | | | | |
|---|---|---|---|---|
| 2014/0008672 | A1* | 1/2014 | Takao | H01L 27/15 |
| | | | | 257/89 |
| 2016/0143520 | A1* | 5/2016 | Masaki | A61B 1/00009 |
| | | | | 600/109 |
| 2017/0188803 | A1* | 7/2017 | Yabe | F21K 9/64 |
| 2017/0231480 | A1* | 8/2017 | Yamazaki | A61B 1/0002 |
| | | | | 600/476 |
| 2019/0387964 | A1* | 12/2019 | Kobayashi | A61B 1/0655 |
| 2021/0022592 | A1* | 1/2021 | Yamazaki | H04N 7/18 |
| 2021/0059503 | A1* | 3/2021 | Tanaka | H04N 5/2354 |
| 2021/0400181 | A1* | 12/2021 | Taniguchi | H04N 9/68 |

* cited by examiner

LIGHT SOURCE DEVICE, MEDICAL OBSERVATION SYSTEM, ILLUMINATION METHOD, AND COMPUTER READABLE RECORDING MEDIUM This application claims priority from Japanese Application No. 2019-051418, filed on Mar. 19, 2019, the contents of which are incorporated by reference herein in its entirety.

BACKGROUND

The present disclosure relates to a light source device, a medical observation system, an illumination method, and a computer readable recording medium.

In an endoscope system, in some cases, white light is intermittently emitted and vocal cords of a subject such as a human being or an animal are observed with white illumination light. As an endoscope system for observing the vocal cords of the subject, a technique of emitting pulsed white light in synchronization with the vibration frequency of the vocal cords is known (see, for example, JP 6249909 B2). In this technique, a pulse width of white light is calculated based on a brightness evaluation value that evaluates brightness of an image generated by an imaging unit and an afterimage evaluation value that evaluates the size of an afterimage in the image, and a light source is controlled to emit pulsed light with this pulse width.

SUMMARY incidentally, in recent years, in endoscope systems, vocal cords of a subject are observed with white light by simultaneously emitting red, green, and blue LED (Light Emitting Diode) elements at a predetermined ratio of light emission amounts and combining these.

However, as in JP 6249909 B2 described above, when each of the red, green, and blue LED elements is caused to emit light in synchronization with the vibration frequency of the vocal cords, there is a problem in that, if the light emission time of each LED element is too short, the light amount sensor may not accurately detect the light emission amounts of LED elements due to noise or the like, and the ratio of the light emission amounts of each of red, green, and blue loses, so that the color balance of white light loses.

According to one aspect of the present disclosure, there is provided a light source device including: a plurality of light sources configured to intermittently emit light beams having different wavelength bands from each other; a detector configured to detect light amounts of the light beams emitted by the plurality of light sources; and a processor including hardware, the processor being configured to: control the plurality of light sources to emit the light beams by applying a pulse current with a pulse width larger than a predetermined pulse width to the plurality of light sources before the processor makes a shift to a strobe observation mode of causing the plurality of light sources to emit the light beams by applying a pulse current with the predetermined pulse width to the plurality of light sources while synchronizing an observation mode of the light source device with a vibration frequency of sound input from an outside; set a pulse current value at which a ratio of the light amounts of the light beams emitted by the plurality of light sources becomes a predetermined ratio for the plurality of light sources based on a detection result detected by the detector under a state where the pulse current with the pulse width larger than the predetermined pulse width is applied to the plurality of light sources; and make the shift to the strobe observation mode while maintaining the pulse current value for realizing the predetermined ratio.

DETAILED DESCRIPTION

Figure 1:
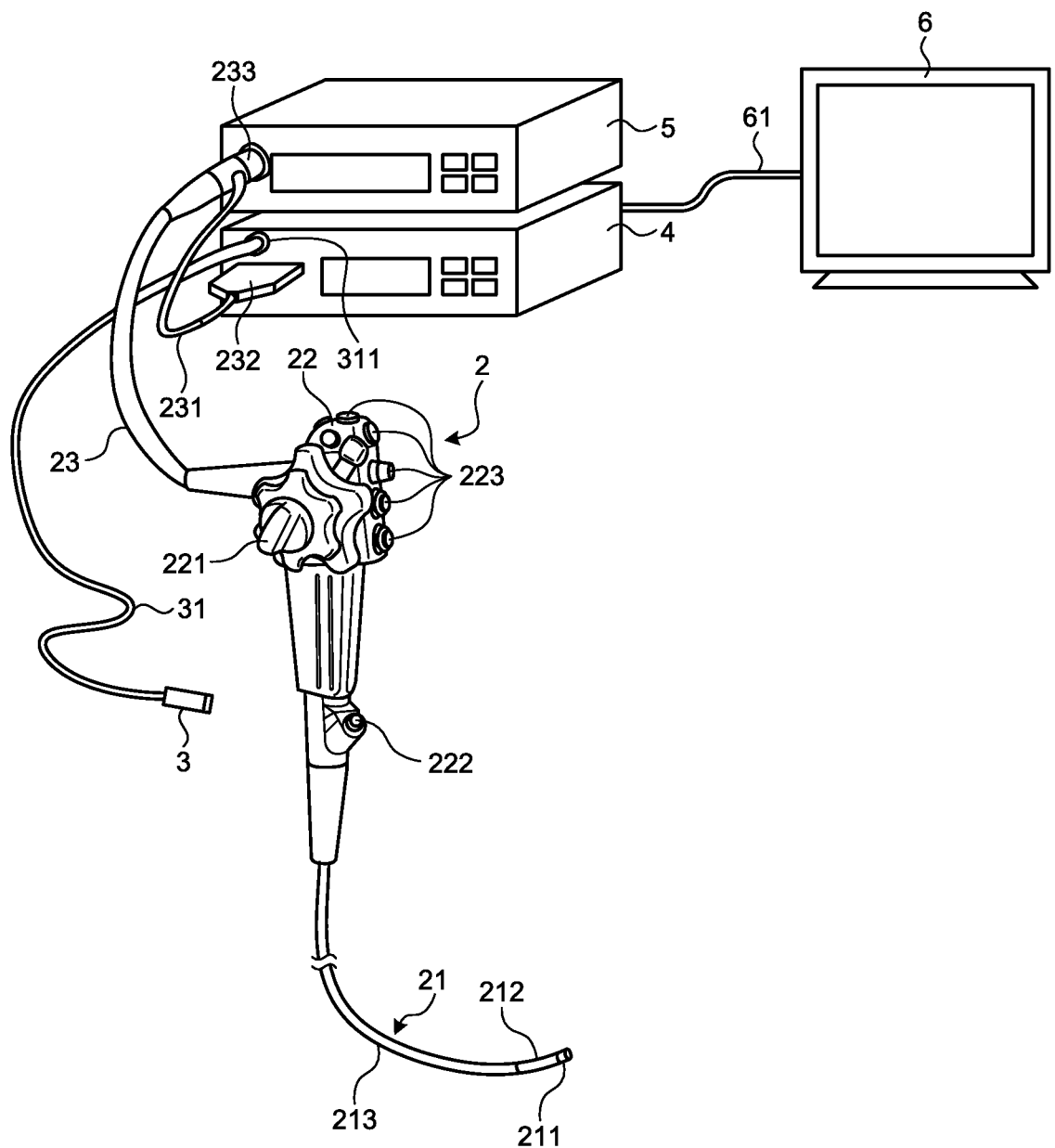
FIG. 1 is a schematic diagram illustrating a schematic configuration of an endoscope system according to an embodiment.

Hereinafter, modes for carrying out the present disclosure (hereinafter referred to as an "embodiment") will be described in detail with reference to the drawings. Note that the present disclosure is not limited to the following embodiments. In addition, each drawing referred to in the following description merely schematically illustrates the shape, size, and positional relationship to the extent that the contents of the present disclosure can be understood. That is, the present disclosure is not limited only to the shape, size, and positional relationship illustrated in each drawing. Further, in the description of the drawings, the same portions are denoted by the same reference numerals for description. Furthermore, an endoscope system will be described as an example of a medical observation system according to the present disclosure. Further, in the description of the drawings, the same portions are denoted by the same reference numerals for description.

Configuration of Endoscope System

FIG. 1 is a schematic diagram illustrating a schematic configuration of an endoscope system according to an embodiment. An endoscope system 1 illustrated in FIG. 1 is used in the medical field, and is a device that is inserted into the oral cavity or inside (in vivo) of a subject such as a human or animal living body and observes the subject by displaying an image obtained by imaging the inside or vocal cords. In the embodiment, a flexible endoscope system will be described as the endoscope system 1. However, the endoscope system 1 is not limited thereto, and may be a rigid endoscope system, for example.

The endoscope system 1 illustrated in FIG. 1 includes an endoscope 2 that is introduced into the oral cavity of a subject and captures the vocal cords and oral cavity of the subject to generate an imaging signal in the subject, a sound input device 3 to which sound emitted from the subject is input, a control device 4 that performs predetermined image processing on an imaging signal generated by the endoscope 2 and controls each portion of the endoscope system 1, a light source device 5 that supplies illumination light emitted to the subject to the endoscope 2, and a display device 6 that displays an image corresponding to an image signal generated by the control device 4 performing image processing.

The endoscope 2 includes an insertion portion 21 to be inserted into a subject, an operating unit 22 on the proximal end side of the insertion portion 21 and held by an operator, and a flexible universal code 23 extending from the operating unit 22.

The insertion portion 21 is realized using an illumination fiber (light guide cable), an electric cable, or the like. The insertion portion 21 includes a distal end portion 211 including an imaging unit incorporating an imaging element that captures the inside of a subject, a bending portion 212 that is bendable and is configured by a plurality of bending pieces, and a flexible tube portion 213 that has flexibility and is provided on a proximal end side of the bending portion 212. The distal end portion 211 has an illumination unit that illuminates the inside of the subject via an illumination lens, an observation unit that captures the inside of the subject, an opening that communicates a processing tool channel, and an air/water supply nozzle (not illustrated).

The operating unit 22 includes a bending knob 221 that bends the bending portion 212 in the vertical direction and the left-right direction, a treatment tool insertion portion 222 from which a treatment tool such as a biological forceps or a laser knife is inserted into the body cavity of the subject, and a plurality of switch units 223 that operate peripheral devices such as the control device 4, the light source device 5, an air supply device, a water supply device, and a gas supply device. The treatment tool inserted from the treatment tool insertion portion 222 is exposed from the opening at the distal end of the insertion portion 21 through a treatment tool channel provided inside.

The universal cord 23 is configured using an illumination fiber, an electric cable, and the like. The universal cord 23 is branched at the proximal end, and one end portion of a branching cord 231 that is branched therefrom is a connector 232 and the other proximal end is a connector 233. The connector 232 is detachable from the control device 4. The connector 233 is detachable from the light source device 5. The universal cord 23 propagates the illumination light emitted from the light source device 5 to the distal end portion 211 via the connector 232, the operating unit 22, and the flexible tube portion 213. The universal code 23 transmits an imaging signal generated by the imaging unit provided at the distal end portion 211 to the control device 4.

The insertion portion 21 and the universal cord 23 are provided with an illumination fiber 214 (see FIG. 2) that guides illumination light from the light source device 5. One end of the illumination fiber 214 is located on the distal end surface of the insertion portion 21, and the other end is located on the connection plane of the universal cord 23 with the light source device 5.

The sound input device 3 receives a sound emitted from the vocal cords of a subject. A cord 31 has a distal end connected to the sound input device 3, and a connector 311 at the proximal end is detachable from the control device 4. The sound input device 3 outputs the input sound to the control device 4 via the cord 31 and the connector 311. The sound input device 3 includes a microphone, an A/D conversion circuit, a gain-up circuit, and the like.

The control device 4 performs predetermined image processing on the imaging signal input from the endoscope 2 via the universal code 23 to generate an image signal, and outputs the image signal to the display device 6. The control device 4 controls each unit of the endoscope system 1 based on various instruction signals transmitted from the switch units 223 in the operating unit 22 of the endoscope 2 via the universal cord 23.

The light source device 5 emits white light combined by emitting light of red, green, and blue at the same time, or special light used for NBI (Narrow Band Imaging) observation and infrared light observation to the endoscope 2 via the connector 232 and the universal cord 23, under the control of the control device 4. The light source device 5 and the control device 4 may be configured to communicate individually as illustrated in FIG. 1, or may be configured to be integrated.

The display device 6 displays an image corresponding to the image signal input from the control device 4 via a video cable 61. The display device 6 displays various types of information related to the endoscope system 1. The display device 6 is configured using a display using liquid crystal or organic EL (Electro Luminescence).

Detailed Configurations of Endoscope, Control Device, and Light Source Device

Figure 2:
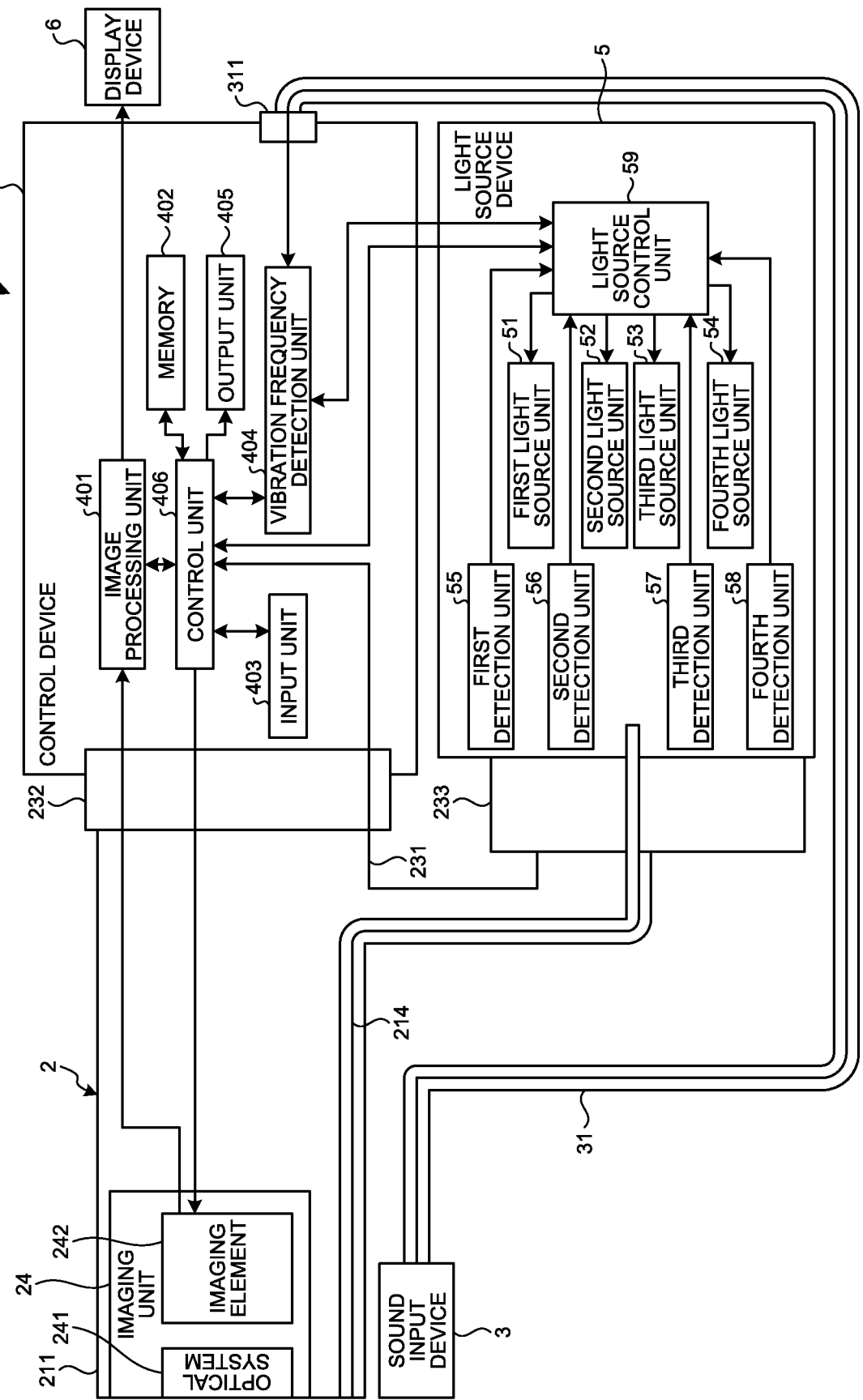
FIG. 2 is a block diagram illustrating functional configurations of an endoscope, a control device, and a light source device included in the endoscope system according to the embodiment.

Next, detailed functional configurations of the endoscope 2, the control device 4, and the light source device 5 will be described. FIG. 2 is a block diagram illustrating functional configurations of the endoscope 2, the control device 4, and the light source device 5 included in the endoscope system 1.

Configuration of Endoscope

First, the configuration of the endoscope 2 will be described.

The endoscope 2 includes at least an imaging unit 24. The imaging unit 24 includes an optical system 241 and an imaging element 242.

The optical system 241 is configured using one or a plurality of lenses, and forms a subject image on the light receiving surface of the imaging element 242.

The imaging element 242 receives the subject image formed by the optical system 241 and outputs an imaging signal generated by performing photoelectric conversion to the control device 4 via a transmission cable of the universal code 23 and the connector 232.

Configuration of Control Device

Next, the configuration of the control device 4 will be described.

The control device 4 includes an image processing unit 401, a memory 402, an input unit 403, a vibration frequency detection unit 404, an output unit 405, and a control unit 406.

The image processing unit 401 performs predetermined image processing on the imaging signal input from the endoscope 2 to generate an image signal, and outputs the image signal to the display device 6, under the control of the control unit 406. Here, the predetermined image processing is image processing including at least A/D conversion processing, gain adjustment processing, optical black subtraction processing, white balance (WB) adjustment processing, synchronization processing when the imaging element 242 is a Bayer array, color matrix processing, gamma correction processing, color reproduction processing, edge enhancement processing, and the like. The image processing unit 401 is configured using a memory and a processor having hardware such as an FPGA (Field Programmable Gate Array), an ASIC (Application Specific Integrated Circuit), and a GPU (Graphics Processing Unit).

The memory 402 is configured using a volatile memory, a nonvolatile memory, a frame memory, and the like. The memory 402 stores various programs executed by the endoscope system 1 and various types of data used during processing. The memory 402 may further include a memory card that may be attached to the control device 4.

The input unit 403 is configured using a keyboard, a mouse, a touch panel, and the like. The input unit 403 receives input of various types of information by user operations.

The vibration frequency detection unit 404 detects the frequency (sound band frequency) of the sound data input from the sound input device 3 via the cord 31 and the connector 311, and outputs the detection result to the control unit 406 and the light source device 5. This sound data is generated from the vocal cords of a subject.

The output unit 405 is configured using a speaker, a printer, a display, and the like. The output unit 405 outputs various types of information related to the endoscope system 1 under the control of the control unit 406.

The control unit 406 comprehensively controls each unit constituting the endoscope system 1. The control unit 406 is configured using a memory and a processor having hardware such as a CPU (Central Processing Unit).

Configuration of Light Source Device

Next, the configuration of the light source device 5 will be described.

The light source device 5 includes a first light source unit 51, a second light source unit 52, a third light source unit 53, a fourth light source unit 54, a first detection unit 55, a second detection unit 56, a third detection unit 57, a fourth detection unit 58, and a light source control unit 59.

The first light source unit 51 emits light in a red wavelength band (wavelength band of 600 nm to 700 nm) to be supplied to the illumination fiber 214 of the endoscope 2 under the control of the light source control unit 59. The first light source unit 51 performs pulse emission with a pulse width of a pulse current applied from the light source control unit 59, and performs pulse emission with a light emission amount corresponding to the pulse current value. The first light source unit 51 is configured using a semiconductor laser element or a light emitting LED (Light Emitting Diode) capable of emitting red light, a lens, a mirror, and the like.

The second light source unit 52 emits light in a green wavelength band (wavelength band of 500 nm to 600 nm) to be supplied to the illumination fiber 214 of the endoscope 2 under the control of the light source control unit 59. The second light source unit 52 performs pulse emission with a pulse width of a pulse current applied from the light source control unit 59, and performs pulse emission with a light emission amount corresponding to the pulse current value. The second light source unit 52 is configured using a semiconductor laser element or a light emitting LED capable of emitting green light, a lens, a mirror, and the like.

The third light source unit 53 emits light in a blue wavelength band (wavelength band of 400 nm to 500 nm) to be supplied to the illumination fiber 214 of the endoscope 2 under the control of the light source control unit 59. The third light source unit 53 performs pulse emission with a pulse width of a pulse current applied from the light source control unit 59, and performs pulse emission with a light emission amount corresponding to the pulse current value. The third light source unit 53 is configured using a semiconductor laser element or a light emitting LED capable of emitting blue light, a lens, a mirror, and the like.

The fourth light source unit 54 emits light in a purple wavelength band (wavelength band of 390 nm to 425 nm) to be supplied to the illumination fiber 214 of the endoscope 2 under the control of the light source control unit 59. The fourth light source unit 54 performs pulse emission with a pulse width of a pulse current applied from the light source control unit 59, and performs pulse emission with a light emission amount corresponding to the pulse current value. The fourth light source unit 54 is configured using a semiconductor laser element or a light emitting LED capable of emitting purple light, a lens, a mirror, and the like. In the embodiment, the fourth light source unit 54 emits light in a purple wavelength band. However, for example, amber light may be emitted. As a matter of course, in the embodiment, the light source device 5 may emit four types of light, but the type of color and the number of colors are not limited. For example, the light source device 5 may emit six types of light including infrared light and amber light.

The first detection unit 55 is arranged at a position where the light emitted by the first light source unit 51 may be detected, detects the intensity of the light emitted by the first light source unit 51, and outputs the detection result to the light source control unit 59. The first detection unit 55 is configured using an optical sensor such as a photodiode.

The second detection unit 56 is arranged at a position where the light emitted by the second light source unit 52 may be detected, detects the intensity of the light emitted by the second light source unit 52, and outputs the detection result to the light source control unit 59. The second detection unit 56 is configured using an optical sensor such as a photodiode.

The third detection unit 57 is arranged at a position where the light emitted by the third light source unit 53 may be detected, detects the intensity of the light emitted by the third light source unit 53, and outputs the detection result to the light source control unit 59. The third detection unit 57 is configured using an optical sensor such as a photodiode.

The fourth detection unit 58 is arranged at a position where the light emitted by the fourth light source unit 54 may be detected, detects the intensity of the light emitted by the fourth light source unit 54, and outputs the detection result to the light source control unit 59. The fourth detection unit 58 is configured using an optical sensor such as a photodiode.

The light source control unit 59 includes: a memory; and at least one processor such as a CPU and FPGA hardware, etc. The light source control unit 59 causes the first light source unit 51, the second light source unit 52, and the third light source unit 53 to emit light by applying a pulse current value with a predetermined pulse width thereto based on the control signal input from the control unit 406, to thereby emit white illumination light toward the illumination fiber 214 of the endoscope 2. The light source control unit 59 causes the first light source unit 51, the second light source unit 52, and the third light source unit 53 to emit light by applying a pulse current with a pulse width larger than a predetermined pulse width thereto before the light source control unit 59 makes the shift to a strobe observation mode of causing the first light source unit 51, the second light source unit 52, and the third light source unit 53 to emit light by applying a pulse current with the predetermined pulse width thereto while synchronizing an observation mode of the light source device 5 with a frequency cycle of sound input from the control device 4. Then, under a state where a pulse current with a pulse width larger than a predetermined pulse width is applied to the first light source unit 51, the second light source unit 52, and the third light source unit 53, the light source control unit 59 sets a pulse current value at which the ratio of the light amounts of light beams emitted by the first light source unit 51, the second light source unit 52, and the third light source unit 53 becomes a predetermined ratio for the first light source unit 51, the second light source unit 52, and the third light source unit 53 based on the detection result detected by any one or more of the first detection unit 55, the second detection unit 56, and the third detection unit 57. Subsequently, the light source control unit 59 makes the shift to the strobe observation mode by setting the pulse width of the pulse current applied to the first light source unit 51, the second light source unit 52, and the third light source unit 53 to a predetermined pulse width while maintaining the pulse current value at which the ratio of the light amounts of light beams emitted by the first light source unit 51, the second light source unit 52, and the third light source unit 53 becomes the predetermined ratio. Then, before the light source control unit 59 makes the shift of the observation mode of the light source device 5 to the strobe observation mode, the light source control unit 59 applies a pulse current with a pulse width larger than a predetermined pulse width to the first light source unit 51, the second light source unit 52, and the third light source unit 53 at every predetermined timing, and sets a pulse current value for the first light source unit 51, the second light source unit 52, and the third light source unit 53 based on the detection result detected by any one or more of the first detection unit 55, the second detection unit 56, and the third detection unit 57. In addition, when the light source control unit 59 makes the shift from another observation mode in which the pulse width and the pulse current value may be changed at every predetermined timing to the strobe observation mode, the light source control unit 59 makes the shift from the another observation mode to a state where a pulse current with a pulse width larger than a predetermined pulse width is applied to the first light source unit 51, the second light source unit 52, and the third light source unit 53. In the embodiment, the light source control unit 59 functions as a processor.

Processing Executed by Light Source Device

Figure 3:
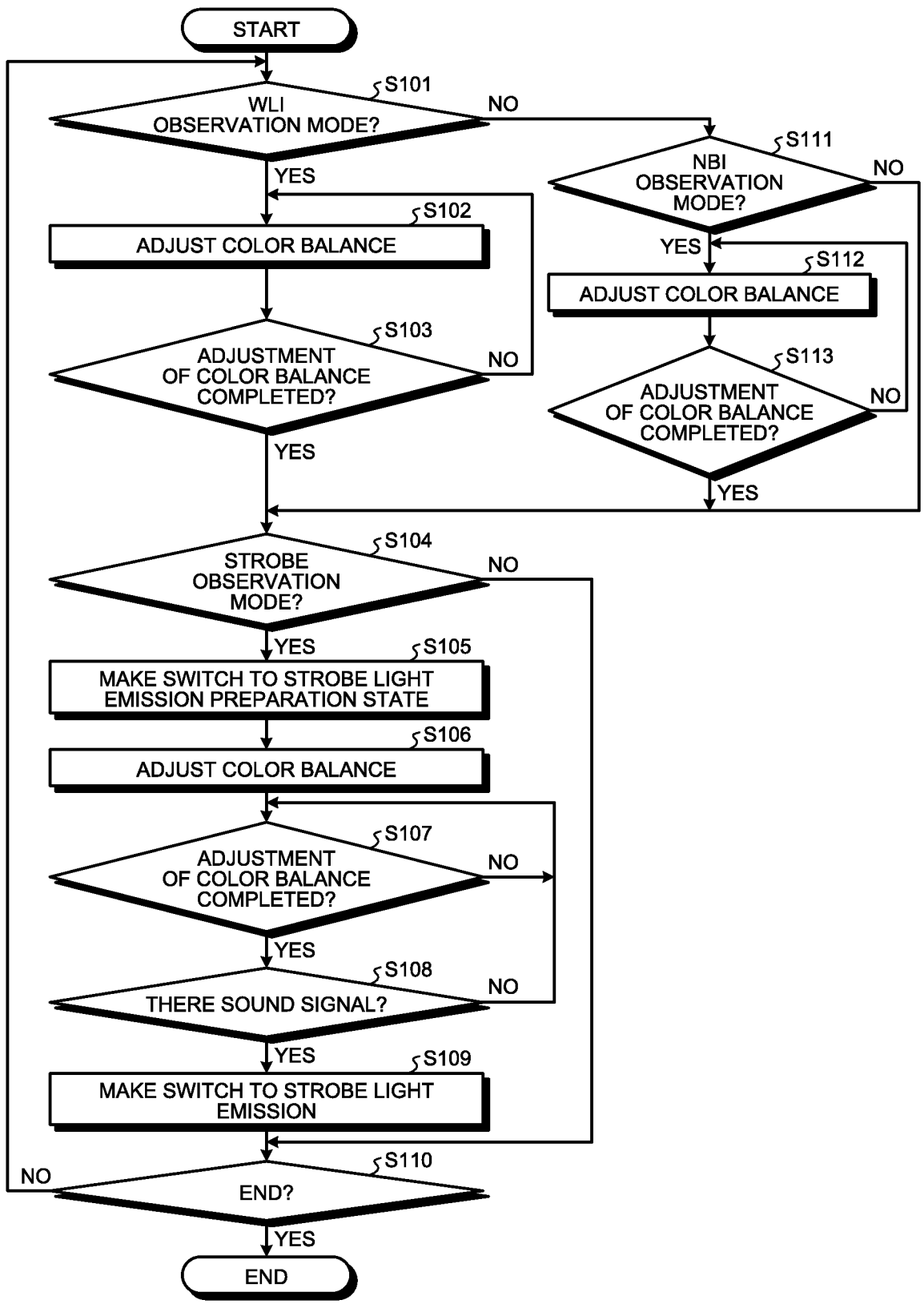
FIG. 3 is a flowchart illustrating an outline of processing executed by the light source device according to the embodiment.

Next, processing executed by the light source device 5 will be described. FIG. 3 is a flowchart illustrating an outline of processing executed by the light source device 5.

As illustrated in FIG. 3, first, description is made of the case where it is determined by the light source control unit 59 that the observation mode of the endoscope system 1 is a WLI (White Light Imaging) observation mode for observing a subject with white light (Step S101: Yes). In this case, in order to emit white light, the light source control unit 59 adjusts the color balance of performing adjustment so that the light amounts of light beams emitted by the first light source unit 51, the second light source unit 52, and the third light source unit 53 has a predetermined ratio (Step S102).

Figure 4:
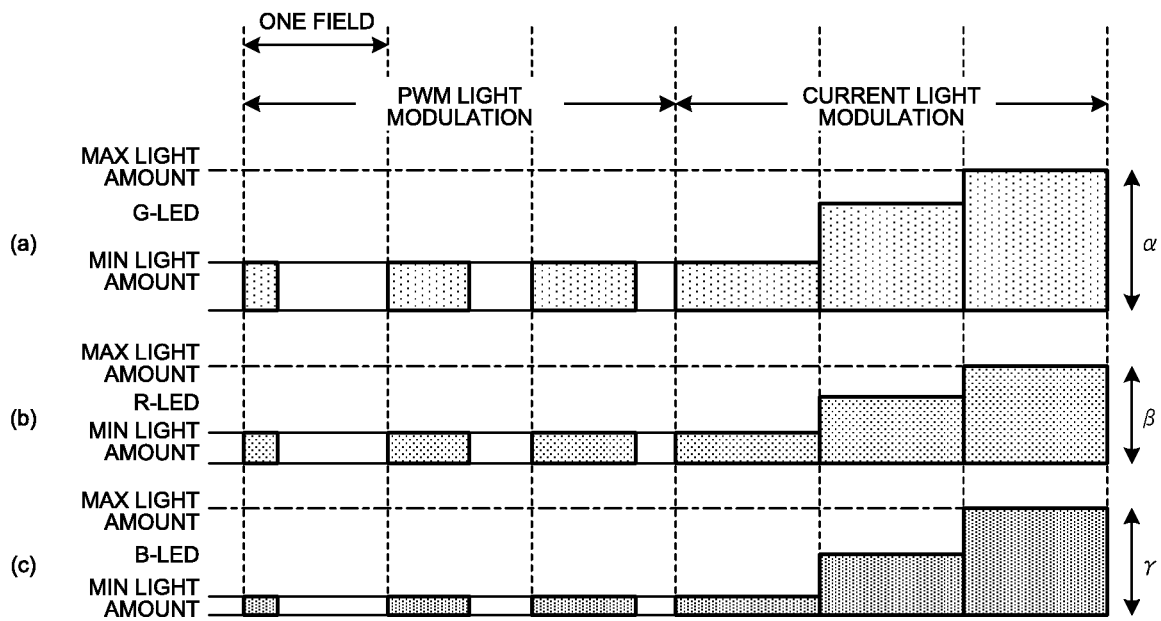
FIG. 4 is a diagram schematically illustrating an outline of color balance adjustment performed by a light source control unit in a WLI observation mode according to the embodiment.

FIG. 4 is a diagram schematically illustrating an outline of color balance adjustment performed by the light source control unit 59 in the WLI observation mode. In FIG. 4, the horizontal axis indicates time, and the vertical axis indicates the light amount. Further, in FIG. 4, (a) from the top illustrates the light amount and the pulse width of the second light source unit 52, (b) illustrates the light amount and the pulse width of the first light source unit 51, and (c) illustrates the light amount and the pulse width of the third light source unit 53. In the following description, the light amounts of light emitted by the first light source unit 51, the second light source unit 52, and the third light source unit 53 are described as $\alpha$, $\beta$, and $\gamma$.

As illustrated in FIG. 4, the light source control unit 59 causes the first light source unit 51, the second light source unit 52, and the third light source unit 53 to emit light for each feed (at every predetermined timing) at which the imaging element 242 of the endoscope 2 generates an imaging signal. In this case, the light source control unit 59 causes the first light source unit 51, the second light source unit 52, and the third light source unit 53 to emit light so that the red, green, and blue light beams are combined (synthesized) into white light based on the detection results of the first detection unit 55, the second detection unit 56, and the third detection unit 57. Specifically, the light source control unit 59 controls the pulse current value and the pulse width applied to the first light source unit 51, the second light source unit 52, and the third light source unit 53 so that the ratio of the light amounts ($\alpha$, $\beta$, and $\gamma$) emitted by the first light source unit 51, the second light source unit 52, and the third light source unit 53 becomes a constant ratio based on the detection results of the first detection unit 55, the second detection unit 56, and the third detection unit 57.

For example, the light source control unit 59 adjusts the color balance so that the light obtained by the combination of red, green, and blue becomes white light by changing the pulse current value or the pulse width applied to the first light source unit 51 and the third light source unit 53 at a constant rate with respect to the light amount of green emitted by the second light source unit 52 based on the detection results of the first detection unit 55, the second detection unit 56, and the third detection unit 57. More specifically, the light source control unit 59 adjusts the color balance by adjusting the current value applied to each of the first light source unit 51, the second light source unit 52, and the third light source unit 53 based on the detection results of the first detection unit 55, the second detection unit 56, and the third detection unit 57. In this case, the light source control unit 59 adjusts the color balance by performing PWM (Pulse Width Modulation) control of adjusting the pulse width of the pulse current applied to each of the first light source unit 51, the second light source unit 52, and the third light source unit 53 when a light emission amount at which the current value that may be applied to each of the first light source unit 51, the second light source unit 52, and the third light source unit 53 becomes the minimum value is the minimum value (MIN light amount). Thereby, when performing the WLI observation mode, the endoscope system 1 may observe a subject in a state where the color balance of light beams emitted by the first light source unit 51, the second light source unit 52, and the third light source unit 53 is adjusted.

Returning to FIG. 3, the description subsequent to Step S103 is continued.

In Step S103, when the light source control unit 59 determines that the adjustment of the color balance of the light amounts emitted by the first light source unit 51, the second light source unit 52, and the third light source unit 53 is completed based on the detection results of the first detection unit 55, the second detection unit 56, and the third detection unit 57 (Step S103: Yes), the light source device 5 proceeds to Step S104 described later. On the other hand, when the light source control unit 59 does not complete the adjustment of the color balance of the light amounts emitted by the first light source unit 51, the second light source unit 52, and the third light source unit 53 based on the detection results of the first detection unit 55, the second detection unit 56, and the third detection unit 57 (Step S103: No), the light source device 5 returns to Step S102 described above.

In Step S104, the light source control unit 59 determines whether or not an instruction signal for switching from the WLI observation mode to the strobe observation mode is input from the input unit 403 of the control device 4 or the switch unit 223 of the endoscope 2. When it is determined by the light source control unit 59 that the instruction signal for switching from the WLI observation mode to the strobe observation mode is input from the input unit 403 of the control device 4 (Step S104: Yes), the light source device 5 proceeds to Step S105 described later. On the other hand, when it is determined by the light source control unit 59 that the instruction signal for switching from the WLI observation mode to the strobe observation mode is not input from the input unit 403 of the control device 4 or the switch unit 223 of the endoscope 2 (Step S104: No), the light source device 5 proceeds to Step S110 described later.

In Step S105, the light source control unit 59 switches the current value and the pulse width of the pulse current applied to each of the first light source unit 51, the second light source unit 52, and the third light source unit 53 to a strobe light emission preparation state.

Subsequently, the light source control unit 59 adjusts the color balance in the strobe observation mode (Step S106). After Step S106, the light source device 5 proceeds to Step S107 described later.

Figure 5:
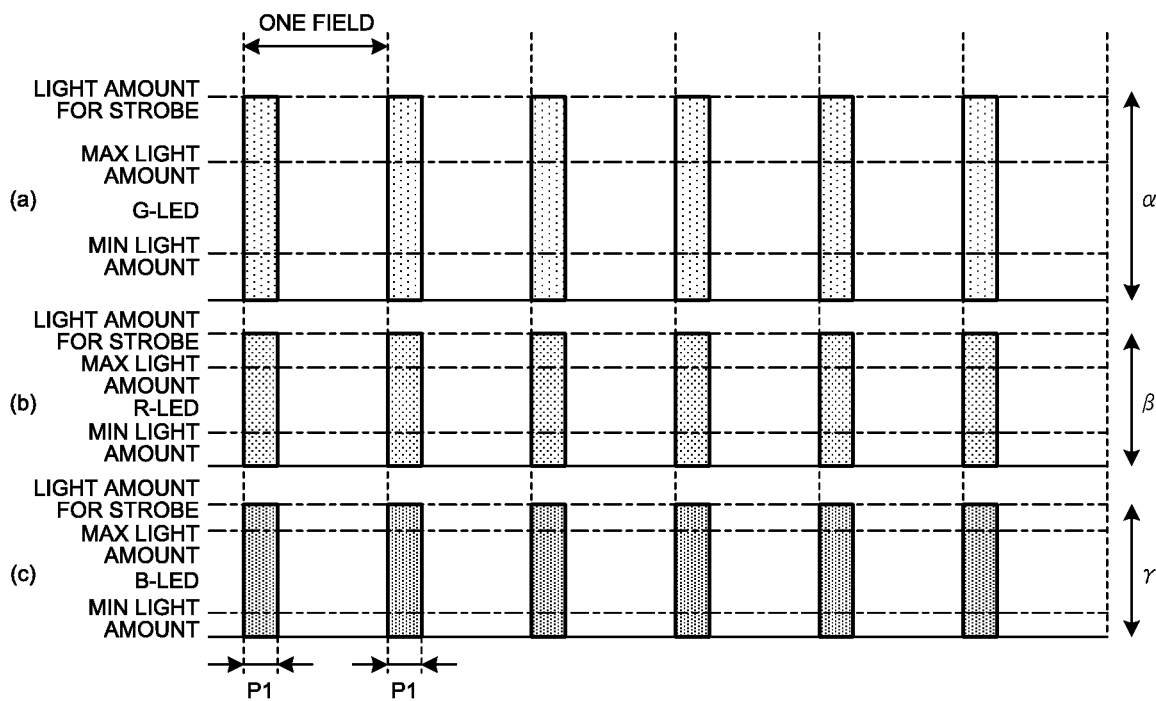
FIG. 5 is a diagram schematically illustrating an outline of color balance adjustment performed in a strobe light emission preparation state before the light source control unit makes a shift to a strobe observation mode according to the embodiment.

FIG. 5 is a diagram schematically illustrating an outline of color balance adjustment performed in the strobe light emission preparation state before the light source control unit 59 makes the shift to the strobe observation mode. In FIG. 5, the horizontal axis indicates time, and the vertical axis indicates the light amount. Further, in FIG. 5, (a) from the top illustrates the light amount and the pulse width of the second light source unit 52, (b) illustrates the light amount and the pulse width of the first light source unit 51, and (c) illustrates the light amount and the pulse width of the third light source unit 53.

As illustrated in FIG. 5, the light source control unit 59 applies the current to the first light source unit 51, the second light source unit 52, and the third light source unit 53 while increasing the current value so that the light amount becomes the overdrive light amount (MAX light amount) that exceeds the light amount having the maximum value in the WLI observation mode for each feed (at every predetermined timing) at which the imaging element 242 of the endoscope 2 generates an imaging signal. Further, the light source control unit 59 applies the pulse current with a pulse width larger than the pulse width of the pulse current applied to the first light source unit 51, the second light source unit 52, and the third light source unit 53 in the strobe observation mode described later (for example, about 2 msec). In this case, the light source control unit 59 adjusts the color balance by controlling the current value applied to the first light source unit 51, the second light source unit 52, and the third light source unit 53 so that the ratio of the light amounts (α, β, and γ) emitted by the first light source unit 51, the second light source unit 52, and the third light source unit 53 becomes a constant ratio based on the detection results of the first detection unit 55, the second detection unit 56, and the third detection unit 57. Then, under a state where a pulse current with a pulse width larger than a predetermined pulse width is applied to the first light source unit 51, the second light source unit 52, and the third light source unit 53, the light source control unit 59 sets a pulse current value at which the ratio of the light amounts (α, β, and γ) emitted by the first light source unit 51, the second light source unit 52, and the third light source unit 53 becomes a constant ratio for the first light source unit 51, the second light source unit 52, and the third light source unit 53 based on the detection result detected by any one or more of the first detection unit 55, the second detection unit 56, and the third detection unit 57.

Further, as illustrated in FIG. 5, before the light source control unit 59 makes the shift of the observation mode of the light source device 5 to the strobe observation mode, the light source control unit 59 applies a pulse current with a pulse width larger than a predetermined pulse width to the first light source unit 51, the second light source unit 52, and the third light source unit 53 for each feed (at every predetermined timing), and sets a pulse current value for the first light source unit 51, the second light source unit 52, and the third light source unit 53 based on the detection result detected by any one or more of the first detection unit 55, the second detection unit 56, and the third detection unit 57. Further, when the light source control unit 59 makes the shift from the WLI observation mode in which the pulse width and the pulse current value may be changed at every predetermined timing to the strobe observation mode, the light source control unit 59 makes the shift from the WLI observation mode to a state where a pulse current with a pulse width larger than a predetermined pulse width is applied to the first light source unit 51, the second light source unit 52, and the third light source unit 53.

In one embodiment, under a state where a pulse current with a pulse width larger than a predetermined pulse width is applied to the first light source unit 51, the second light source unit 52, and the third light source unit 53, the light source control unit 59 sets a pulse current value at which the ratio of the light amounts (α, β, and γ) emitted by the first light source unit 51, the second light source unit 52, and the third light source unit 53 becomes a constant ratio for the first light source unit 51, the second light source unit 52, and the third light source unit 53 based on the detection result detected by any one or more of the first detection unit 55, the second detection unit 56, and the third detection unit 57. However, for example, the light source control unit 59 may set a pulse current value at which the ratio of the light amounts (α, β, and γ) emitted by the first light source unit 51, the second light source unit 52, and the third light source unit 53 becomes a constant ratio for the first light source unit 51, the second light source unit 52, and the third light source unit 53 based on the detection results of the first detection unit 55, the second detection unit 56, and the third detection unit 57.

Returning to FIG. 3, the description subsequent to Step S107 is continued.

In Step S107, when the light source control unit 59 determines that the adjustment of the color balance of the light amounts emitted by the first light source unit 51, the second light source unit 52, and the third light source unit 53 is completed based on the detection results of the first detection unit 55, the second detection unit 56, and the third detection unit 57 (Step S107: Yes), the light source device 5 proceeds to Step S108 described later. On the other hand, when the light source control unit 59 does not complete the adjustment of the color balance of the light amounts emitted by the first light source unit 51, the second light source unit 52, and the third light source unit 53 based on the detection results of the first detection unit 55, the second detection unit 56, and the third detection unit 57 (Step S107: No), the light source device 5 returns to Step S106 described above.

In Step S108, the light source control unit 59 determines whether or not a sound signal indicating a frequency cycle of sound is input from the vibration frequency detection unit 404 of the control device 4. When it is determined by the light source control unit 59 that a sound signal indicating a frequency cycle of sound is input from the vibration frequency detection unit 404 of the control device 4 (Step S108: Yes), the light source device 5 proceeds to Step S109 described later. On the other hand, when it is determined by the light source control unit 59 that a sound signal indicating a frequency cycle of sound is not input from the vibration frequency detection unit 404 of the control device 4 (Step S108: No), the light source device 5 returns to Step S106 described above, and the color balance is adjusted in the strobe observation mode until a sound signal indicating a frequency cycle of sound is input from the vibration frequency detection unit 404 of the control device 4. That is, the light source control unit 59 causes the first light source unit 51, the second light source unit 52, and the third light source unit 53 to emit light at every predetermined timing (for each field) until the frequency cycle of sound is input from the vibration frequency detection unit 404 of the control device 4, and sets the pulse current values of the first light source unit 51, the second light source unit 52, and the third light source unit 53 based on a plurality of detection results detected by the first detection unit 55, the second detection unit 56, and the third detection unit 57.

In Step S109, the light source control unit 59 switches the current value and the pulse width of the pulse current applied to each of the first light source unit 51, the second light source unit 52, and the third light source unit 53 to a strobe light emission state. After Step S109, the light source device 5 proceeds to Step S110 described later.

Figure 6:
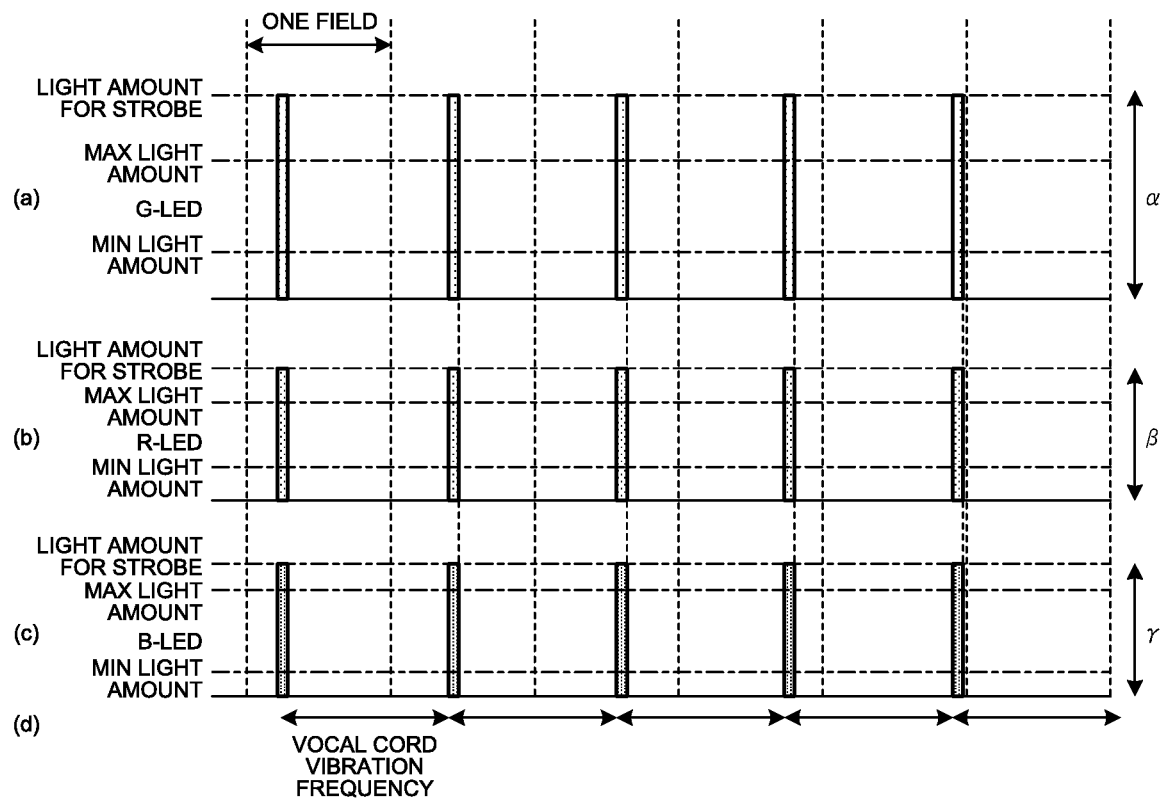
FIG. 6 is a diagram schematically illustrating a strobe emission state performed after the light source control unit makes the shift to the strobe observation mode according to the embodiment.

FIG. 6 is a diagram schematically illustrating the strobe emission state performed after the light source control unit 59 makes the shift to the strobe observation mode. In FIG. 6, the horizontal axis indicates time, and the vertical axis indicates the light amount. Further, in FIG. 6, (a) from the top illustrates the light amount and the pulse width of the second light source unit 52, (b) illustrates the light amount and the pulse width of the first light source unit 51, (c) illustrates the light amount and the pulse width of the third light source unit 53, and (d) illustrates the vibration frequency of the vocal cords.

As illustrated in FIG. 6, the light source control unit 59 causes each of the first light source unit 51, the second light source unit 52, and the third light source unit 53 to emit light by making the pulse width of the pulse current applied to each of the first light source unit 51, the second light source unit 52, and the third light source unit 53 smaller than the pulse width in a strobe light emission sequential state while maintaining the pulse current value at the ratio in which the color balance is adjusted in Step S107 described above. In this case, the light source control unit 59 applies the pulse current to each of the first light source unit 51, the second light source unit 52, and the third light source unit 53 while maintaining the pulse current value at the ratio in which the color balance is adjusted in synchronization with the vibration frequency of the vocal cords. Specifically, the light source control unit 59 causes the first light source unit 51, the second light source unit 52, and the third light source unit 53 to emit light while synchronizing the light emission timings of the first light source unit 51, the second light source unit 52, and the third light source unit 53 with the vibration frequency of the vocal cords. For example, the light source control unit 59 causes the first light source unit 51, the second light source unit 52, and the third light source unit 53 to emit light while synchronizing the light emission timings of the first light source unit 51, the second light source unit 52, and the third light source unit 53 with the timing of the maximum value or the minimum value of the vibration frequency of the vocal cords. Thereby, the light source device 5 may perform the strobe observation on the vocal cords of a subject while maintaining the color balance of white light even when the light emission period of light of each of the first light source unit 51, the second light source unit 52, and the third light source unit 53 is short.

Returning to FIG. 3, the description subsequent to Step S110 is continued.

In Step S110, the light source control unit 59 determines whether or not an instruction signal for ending the observation of the subject is input from the input unit 403 of the control device 4. When it is determined by the light source control unit 59 that an instruction signal for ending the observation of the subject is input (Step S110: Yes), the light source device 5 ends this processing. On the other hand, when it is determined by the light source control unit 59 that an instruction signal for ending the observation of the subject is not input (Step S110: No), the light source device 5 returns to Step S101 described above.

Description is made of the case where it is determined by the light source control unit 59 that the endoscope system 1 is not in the WLI observation mode (Step S101: No) In Step S101. In this case, the light source control unit 59 determines whether or not an instruction signal for instructing the NBI observation mode is input from the input unit 403 of the control device 4 or the switch unit 223 of the endoscope 2 (Step S111). When it is determined by the light source control unit 59 that the instruction signal for instructing the NBI observation mode is input from the input unit 403 of the control device 4 or the switch unit 223 of the endoscope 2 (Step S111: Yes), the light source device 5 proceeds to Step S112 described later. On the other hand, when it is determined by the light source control unit 59 that the instruction signal for instructing the NBI observation mode is not input from the input unit 403 of the control device 4 (Step S111: No), the light source device 5 proceeds to Step S104.

In Step S112, the light source control unit 59 performs color balance adjustment in the NBI observation mode. After Step S112, the light source device 5 proceeds to Step S113.

Figure 7:
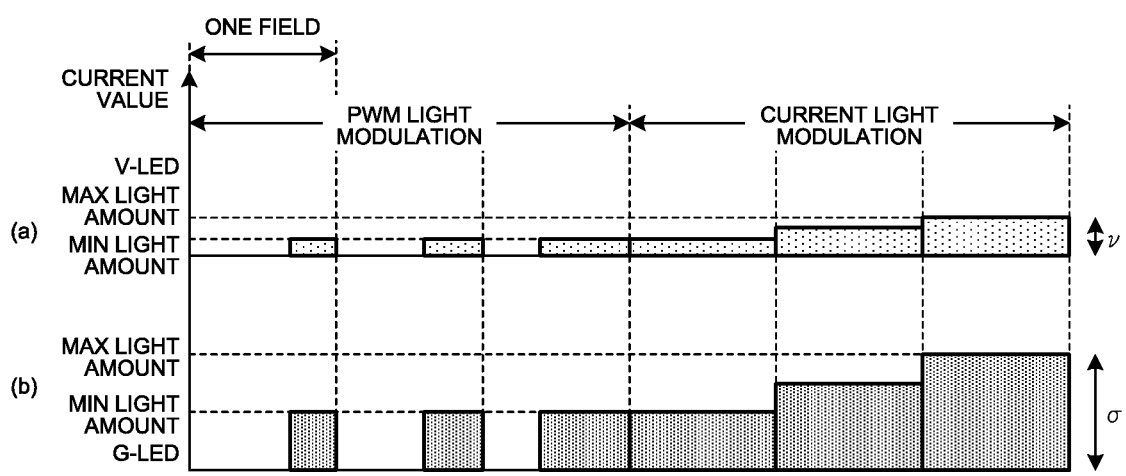
FIG. 7 is a diagram schematically illustrating an outline of color balance adjustment performed by the light source control unit in a NBI observation mode according to the embodiment.

FIG. 7 is a diagram schematically illustrating an outline of color balance adjustment performed by the light source control unit 59 in the NBI observation mode. In FIG. 7, the horizontal axis indicates time, and the vertical axis indicates the amount of light. Further, in FIG. 7, (a) from the top illustrates the light amount and the pulse width of the fourth light source unit 54, and (b) illustrates the light amount and the pulse width of the second light source unit 52. In the following description, the light amounts of light emitted by the second light source unit 52 and the fourth light source unit 54 are described as σ and ν.

As illustrated in FIG. 7, the light source control unit 59 causes the second light source unit 52 and the fourth light source unit 54 to emit light for each feed (for each frame) at which the imaging element 242 of the endoscope 2 generates an imaging signal. In this case, the light source control unit 59 causes the second light source unit 52 and the fourth light source unit 54 to emit light so that the green and purple light beams are combined (synthesized) into narrow band light (for example, the wavelength band of 390 nm to 445 nm+530 nm to 550 nm) in the NBI observation mode based on the detection results of the second detection unit 56 and the fourth detection unit 58. Specifically, the light source control unit 59 controls the pulse current value and the pulse width applied to the second light source unit 52 and the fourth light source unit 54 so that the ratio of the light amounts (σ and ν) emitted by the second light source unit 52 and the fourth light source unit 54 becomes a constant ratio based on the detection results of the second detection unit 56 and the fourth detection unit 58. In this case, the light source control unit 59 adjusts the color balance of narrow band light by performing PWM control of adjusting the pulse width of the pulse current applied to each of the second light source unit 52 and the fourth light source unit 54 when a light emission amount at which the current value that may be applied to each of the second light source unit 52 and the fourth light source unit 54 is the minimum value becomes the minimum value (MIN light amount). Thereby, when performing the NBI observation mode, the endoscope system 1 may observe a subject with narrow band light in which the color balance of light beams emitted by the second light source unit 52 and the fourth light source unit 54 is adjusted.

In Step S113, when the light source control unit 59 determines that the adjustment of the color balance of the light amounts emitted by the first light source unit 51, the second light source unit 52, the third light source unit 53, and the fourth light source unit 54 is completed based on the detection results of the first detection unit 55, the second detection unit 56, the third detection unit 57, and the fourth detection unit 58 (Step S113: Yes), the light source device 5 proceeds to Step S104 described later. On the other hand, when the light source control unit 59 does not complete the adjustment of the color balance of the light amounts emitted by the first light source unit 51, the second light source unit 52, the third light source unit 53, and the fourth light source unit 54 based on the detection results of the first detection unit 55, the second detection unit 56, the third detection unit 57, and the fourth detection unit 58 (Step S113: No), the light source device 5 returns to Step S112 described above.

In the embodiment described above, before the light source control unit 59 makes the shift to the strobe observation mode of causing the first light source unit 51, the second light source unit 52, and the third light source unit 53 to emit light by applying a pulse current with a predetermined pulse width thereto while synchronizing an observation mode of the light source device 5 with a frequency cycle of sound input from the control device 4, the light source control unit 59 causes the first light source unit 51, the second light source unit 52, and the third light source unit 53 to emit light by applying a pulse current with a pulse width larger than the predetermined pulse width thereto, and under a state where a pulse current with a pulse width larger than the predetermined pulse width is applied to the first light source unit 51, the second light source unit 52, and the third light source unit 53, the light source control unit 59 sets a pulse current value at which the ratio of the light amounts of light beams emitted by the first light source unit 51, the second light source unit 52, and the third light source unit 53 becomes a predetermined ratio for the first light source unit 51, the second light source unit 52, and the third light source unit 53 based on the detection result detected by any one or more of the first detection unit 55, the second detection unit 56, and the third detection unit 57. Thus, the light source control unit 59 makes the shift of the observation mode of the light source device 5 to the strobe observation mode while maintaining the pulse current value that may obtain the predetermined ratio, so that the color balance of white light may be maintained.

Further, according to one embodiment, before the light source control unit 59 makes the shift of the observation mode of the light source device 5 to the strobe observation mode, the light source control unit 59 applies a pulse current with a pulse width larger than a predetermined pulse width to the first light source unit 51, the second light source unit 52, and the third light source unit 53 at every predetermined timing, and sets a pulse current value for the first light source unit 51, the second light source unit 52, and the third light source unit 53 based on the detection result detected by any one or more of the first detection unit 55, the second detection unit 56, and the third detection unit 57. Thus, the light source control unit 59 makes the shift of the observation mode of the light source device 5 to the strobe observation mode while maintaining the pulse current value that may obtain the predetermined ratio, so that the color balance of white light may be maintained.

Further, according to the embodiment, when the light source control unit 59 makes the shift from another WLI observation mode in which the pulse width and the pulse current value may be changed at every predetermined timing to the strobe observation mode, the light source control unit 59 makes the shift from the other WLI observation mode to a state where a pulse current with a pulse width larger than a predetermined pulse width is applied to the first light source unit 51, the second light source unit 52, and the third light source unit 53. Thus, the light source control unit 59 makes the shift of the observation mode of the light source device 5 to the strobe observation mode while maintaining the pulse current value that may obtain the predetermined ratio, so that the color balance of white light may be maintained.

Further, according to the embodiment, when the light source control unit 59 makes the shift of the observation mode of the light source device 5 to the strobe observation mode, the light source control unit 59 causes the first light source unit 51, the second light source unit 52, and the third light source unit 53 to emit light at every predetermined timing until the frequency cycle of sound is input from the control device 4, and sets the pulse current values of the first light source unit 51, the second light source unit 52, and the third light source unit 53 based on a plurality of detection results detected by the first detection unit 55, the second detection unit 56, and the third detection unit 57. Thus, the vocal cords of the subject may be observed in a state where a more accurate color balance is maintained.

Further, according to the embodiment, when the light source control unit 59 makes the shift of the observation mode of the light source device 5 from the strobe observation mode to the WLI observation mode or the NBI observation mode, or from the WLI observation mode or the NBI observation mode to the strobe observation mode, the light source control unit 59 causes the first light source unit 51, the second light source unit 52, the third light source unit 53, and the fourth light source unit 54 to emit light by applying a pulse current thereto, and sets the pulse current values of the first light source unit 51, the second light source unit 52, the third light source unit 53, and the fourth light source unit 54 based on the detection results detected by the first detection unit 55, the second detection unit 56, the third detection unit 57, and the fourth detection unit 58. Thus, the subject may be observed while maintaining the color balance in each observation mode.

In the embodiment, description is made of the case where the light source control unit 59 makes the shift of the observation mode of the light source device 5 from the strobe observation mode to the WLI observation mode or the NBI observation mode, or from the WLI observation mode or the NBI observation mode to the strobe observation mode. However, for example, the strobe observation may be performed with narrow band light emitted in the NBI observation mode. In this case, the light source control unit 59 makes switch to a state similar to the strobe emission state that is performed when the WLI observation mode is shifted to the strobe observation mode. Specifically, before the light source control unit 59 makes the shift to the strobe observation mode with narrow band light of causing the second light source unit 52 and the fourth light source unit 54 to emit light by applying a pulse current with a predetermined pulse width thereto in synchronization with a frequency cycle of sound input from the control device 4, the light source control unit 59 causes the second light source unit 52 and the fourth light source unit 54 to emit light by applying a pulse current with a pulse width larger than the predetermined pulse width thereto, and under a state where a pulse current with a pulse width larger than the predetermined pulse width is applied to the second light source unit 52 and the fourth light source unit 54, the light source control unit 59 sets a pulse current value at which the ratio of the light amounts of light beams emitted by the second light source unit 52 and the fourth light source unit 54 becomes a predetermined ratio for the second light source unit 52 and the fourth light source unit 54 based on the detection result detected by any one or more of the second detection unit 56 and the fourth detection unit 58. Thus, the light source control unit 59 makes the shift of the observation mode of the light source device 5 to the strobe observation mode with narrow band light while maintaining the pulse current value that may obtain the predetermined ratio, so that the color balance of with narrow band light may be maintained. Furthermore, when the light source control unit 59 makes the shift from the WLI observation mode to the strobe observation mode with narrow band light, the light source control unit 59 makes the shift to the strobe observation mode with narrow band light after performing the strobe light emission preparation state with narrow band light described above. As a matter of course, when the light source control unit 59 makes the shift from the NBI observation mode to the strobe observation mode with narrow band light, the light source control unit 59 makes the shift to the strobe observation mode with narrow band light after performing the strobe light emission preparation state with narrow band light described above. Thereby, the observation mode of the light source device 5 is shifted to the strobe observation mode with narrow band light while maintaining the pulse current value that may obtain the predetermined ratio, so that the color balance of the narrow band light may be maintained.

Variations may be formed by appropriately combining a plurality of components disclosed in the endoscope system according to the embodiment described above. For example, some components may be deleted from all the components described in the endoscope system according to the embodiment described above. Furthermore, the components described in the endoscope system according to the embodiment described above may be suitably combined.

Further, in the endoscope system according to the embodiment, the "unit" described above may be read as "means", "circuit", and the like. For example, the control unit may be read as control means or a control circuit.

A program to be executed by the endoscope system according to the embodiment is a file data in an installable format or an executable format and is provided by being recorded on a computer-readable recording medium such as a CD-ROM, a flexible disk (FD), a CD-R, a DVD (Digital Versatile Disk), a USB medium, a flash memory, and the like.

Further, the program to be executed by the endoscope system according to the embodiment may be stored on a computer connected to a network such as the Internet and provided by being downloaded via the network.

In the description of the flowchart in this specification, the context of processing between steps is clearly indicated using expressions such as "first", "after", "subsequently", etc. The order of processing required to perform the present disclosure is not uniquely determined by these expressions. That is, the order of processing in the flowchart described in this specification may be changed within a consistent range.

As described above, some of the embodiments of the present application have been described in detail with reference to the drawings. However, these are merely examples. The present disclosure may be carried out in other embodiments to which various modifications and improvements are made based on the knowledge of those skilled in the art including the aspects described in the disclosure section.

According to the present disclosure, there is an effect that the color balance of white light may be maintained when red, green, and blue light beams are emitted in synchronization with a vibration frequency of vocal cords.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A light source device comprising:
   a plurality of light sources configured to intermittently emit light beams having different wavelength bands from each other;
   a detector configured to detect light amounts of the light beams emitted by the plurality of light sources; and
   a processor comprising hardware, the processor being configured to:
   control the plurality of light sources to emit the light beams by applying a pulse current with a pulse width larger than a predetermined pulse width to the plurality of light sources before the processor makes a shift to a strobe observation mode of causing the plurality of light sources to emit the light beams by applying a pulse current with the predetermined pulse width to the plurality of light sources while synchronizing an observation mode of the light source device with a vibration frequency of sound input from an outside;
   set a pulse current value at which a ratio of the light amounts of the light beams emitted by the plurality of light sources becomes a predetermined ratio for the plurality of light sources based on a detection result detected by the detector under a state where the pulse current with the pulse width larger than the predetermined pulse width is applied to the plurality of light sources; and
   make the shift to the strobe observation mode while maintaining the pulse current value for realizing the predetermined ratio.

2. The light source device according to claim 1, wherein the processor is configured to, before the processor makes the shift of the observation mode of the light source device to the strobe observation mode,
   apply the pulse current with the pulse width larger than the predetermined pulse width to the plurality of light sources at every predetermined timing, and set the pulse current value for the plurality of light sources based on the detection result detected by the detector.

3. The light source device according to claim 1, wherein the processor is configured to make a shift from an other observation mode, in which the pulse width and the pulse current value are changeable at every predetermined timing, to the strobe observation mode to the state where the pulse current with the pulse width larger than the predetermined pulse width is applied to the plurality of light sources when the processor makes the shift from the other observation mode.

4. A medical observation system comprising:
an endoscope including
an insertion portion adapted to be inserted into a subject, and
an imaging device configured to generate an imaging signal and arranged at a distal end portion of the insertion portion; and
the light source device according to claim 1, the light source device being configured to supply the light beams to the endoscope.

* * * * *